United States Patent [19]
Kirsch et al.

[11] Patent Number: 5,997,766
[45] Date of Patent: Dec. 7, 1999

[54] HALOVINYLOXY-SUBSTITUTED DIOXANE DERIVATIVES

[75] Inventors: Peer Kirsch, Darmstadt; Kazuaki Tarumi, Seeheim; Joachim Krause, Dieburg, all of Germany

[73] Assignee: Merck Patent Gesellschaft mit Beschrankter Haftung, Germany

[21] Appl. No.: 08/998,074

[22] Filed: Dec. 24, 1997

[51] Int. Cl.⁶ .......................... C09K 19/34; C07D 319/06
[52] U.S. Cl. ...................................... 252/299.61; 549/369
[58] Field of Search ........................ 252/299.61; 549/369

[56] References Cited

U.S. PATENT DOCUMENTS

| | | | |
|---|---|---|---|
| 4,877,548 | 10/1989 | Kitano et al. | 252/299.63 |
| 5,308,537 | 5/1994 | Coates et al. | 252/299.6 |
| 5,364,556 | 11/1994 | Schadt et al. | 252/299.01 |
| 5,403,512 | 4/1995 | Bartmann et al. | 252/299.01 |
| 5,494,606 | 2/1996 | Reiffenrath et al. | 252/299.61 |
| 5,662,828 | 9/1997 | Tsubata et al. | 252/299.61 |
| 5,667,721 | 9/1997 | Buchecker et al. | 252/299.61 |
| 5,707,547 | 1/1998 | Fujimoto et al. | 252/299.61 |
| 5,730,901 | 3/1998 | Shimizu et al. | 252/299.61 |

OTHER PUBLICATIONS

Derwent Abstract of DE 4238377.

Primary Examiner—C. H. Kelly
Attorney, Agent, or Firm—Millen, White, Zelane, & Branigan, P.C.

[57] ABSTRACT

Halovinyloxy-substituted dioxane derivatives of the formula I

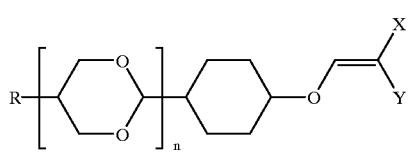

in which R, X, Y and n are as defined in claim 1, are useful as components of liquid-crystalline media, and in liquid-crystal and electro-optical display elements which contain the novel liquid-crystalline media.

18 Claims, No Drawings

HALOVINYLOXY-SUBSTITUTED DIOXANE DERIVATIVES

The invention relates to halovinyloxy-substituted dioxane derivatives of the general formula I

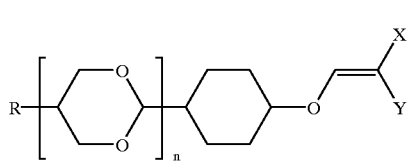

in which
R is alkyl or alkenyl having 1 to 12 carbon atoms, in each of which one or more $CH_2$ groups may be replaced by —O—, —$CF_2$— or —CH=CH—, and one or two CH groups may be replaced by CF, in such a way that two oxygen atoms are not linked to one another,
X and Y are each, independently of one another, H, F or Cl, where, if one of the radicals X and Y is H, the other radical X or Y is F or Cl, and
n is 1, 2 or 3.

The invention furthermore relates to the use of these compounds as components of liquid-crystalline media and to liquid-crystal and electro-optical display elements which contain the novel liquid-crystalline media.

The compounds of the formula I can be used as components of liquid-crystalline media, in particular for displays based on the principle of the twisted cell, the guest-host effect, the effect of deformation of aligned phases or the effect of dynamic scattering.

Difluorovinyl ethers are disclosed, for example in DE 42 38 377, but the difluorovinyl ether group in the compounds described therein is linked to an aromatic ring.

EP 0 325 796 describes liquid-crystalline compounds in which a cyclohexane ring is linked to a difluorovinyl group. However, these compounds have been found to be unstable and tend to decompose with elimination of HF.

The invention therefore had an object of finding novel, stable, liquid-crystalline or mesogenic compounds which are suitable as components of liquid-crystalline media and in particular simultaneously have comparatively low viscosity and are stable to heat and to UV irradiation.

Upon further study of the specification and appended claims, further objects and advantages of this invention will become apparent to those skilled in the art.

It has been found that compounds of the formula I are eminently suitable as components of liquid-crystalline media. In particular, they have high nematogeniety and comparatively low viscosities. The simultaneous use of 1,3-dioxane as a constituent of the mesogenic skeleton and a halovinyloxy group as polar end group results in crystalline compounds of high Δε and very low Δn at the same time as very good viscoelastic properties. They can be used to obtain stable liquid-crystalline media having a broad mesophase range and advantageous optical and dielectric anisotropy values. These media furthermore have very good low-temperature behavior.

In addition, the provision of compounds of the formula I very generally considerably broadens the range of liquid-crystalline substances which are suitable for various applicational points of view for the preparation of liquid-crystalline mixtures.

The compounds of the formula I have a broad range of applications. Depending on the choice of substituents, these compounds can be used as base materials of which liquid-crystalline media are predominantly composed. However, it is also possible to add compounds of the formula I to liquid-crystalline base materials from other classes of compound in order, for example, to modify the dielectric and/or optical anisotropy of a dielectric of this type and/or to optimize its threshold voltage and/or its viscosity.

In the pure state, the compounds of the formula I are colorless and form liquid-crystalline mesophases in a temperature range which is favorably located for electro-optical use. They are stable chemically, thermally and to light.

The invention thus relates to the compounds of the formula I and to the use of these compounds as components of liquid-crystalline media. The invention furthermore relates to liquid-crystalline media containing at least one compound of the formula I and to liquid-crystalline display elements, in particular electro-optical display elements, especially STN and AMD displays, which contain such media.

The compounds of the formula I include the preferred compounds of the subformulae Ia and Ib, in particular

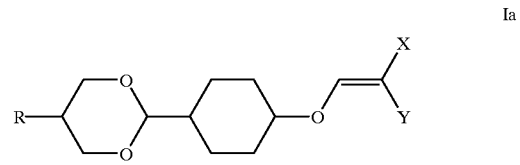

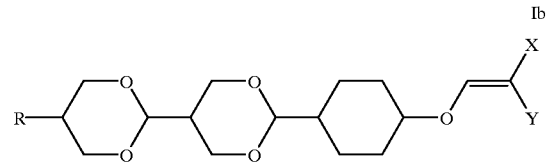

in which R, X and Y are as defined above.

In the compounds of the formula I, n is preferably 1, or furthermore 2. The radical R is preferably a straight-chain alkyl radical, furthermore an alkenyl radical. The halovinyloxy radical preferably has one of the following structures:

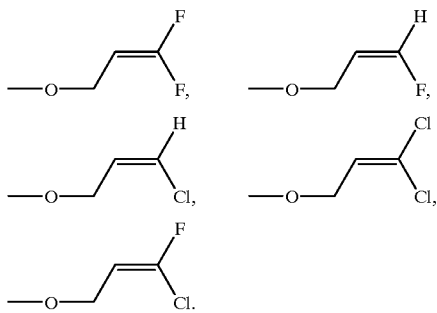

Particular preference is given to compounds in which X=Y=F, and furthermore those in which one of X or Y=F and the other of X or Y=H.

If R is an alkyl radical and/or an alkoxy radical (i.e., where the first —$CH_2$— group is replaced by —O—), it may be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, methoxy, octoxy, nonoxy, decoxy, undecoxy or dodecoxy.

Oxaalkyl is preferably straight-chain 2-oxapropyl (=methoxymethyl), 2-oxabutyl (=ethoxymethyl) or 3-oxybutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl.

If R is an alkenyl radical, this may be straight-chain or branched. It is preferably straight-chain and has 2 to 10 carbon atoms. Accordingly, it is in particular vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl. Particular preference is given to the vinyl group and trans-alk-1-enyl radicals.

If R is an alkyl or alkenyl radical in which one or more $CH_2$ groups have been replaced by $CF_2$, this radical is preferably straight-chain. In the case of multiple substitution, the resultant radicals also include perfluorinated radicals. In the case of monosubstitution, the fluorine substituent can be in any desired position, but is preferably in the ω-position.

In a particularly preferred embodiment, R is 1E-alkenyl, 3-alkenyl, $C_nH_{2+1}$—(CH=CH)$_o$—, $CF_2$=CH—O— or $CF_2$=CF—, where n=1–8 and o is 0 or 1.

Compounds of the formula I containing branched wing groups R may occasionally be of importance owing to better solubility in the conventional liquid-crystal-line base materials, but in particular as chiral dopants if they are optically active. Smectic compounds of this type are suitable as components of ferroelectric materials.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy and 1-methylheptoxy.

The formula I covers both the racemates of these compounds and the optical antipodes, and mixtures thereof.

Of these compounds of the formula I and the subformulae, preference is given to those in which at least one of the radicals present therein has one of the preferred meanings indicated.

In the compounds of the formula I, preference is given to the stereoisomers in which the cyclohexane ring is trans-1,4-disubstituted.

It is self-evident to the person skilled in the art that the formula I also covers the compounds in which the C, H, O, F and Cl atoms have been replaced by the corresponding isotopes $^{13}C$, $^{14}C$, D, T, $^{10}O$, $^{18}O$ and $^{37}Cl$ The compounds of the formula I are prepared by methods known per se, and described in the literature (for example in the standard works, such as Houben-Weyl, Methoden der Organischen Chemie, Georg-Thieme-Verlag, Stuttgart), to be precise under reaction conditions which are known and are suitable for said reactions.

Use can also be made here of variants which are known per se, but are not described here in further detail.

If desired, the starting materials can also be formed in situ by not isolating them from the reaction mixture, but instead immediately converting them into the compounds of the formula I.

The novel compounds can be prepared, for example, in accordance with the following reaction schemes:

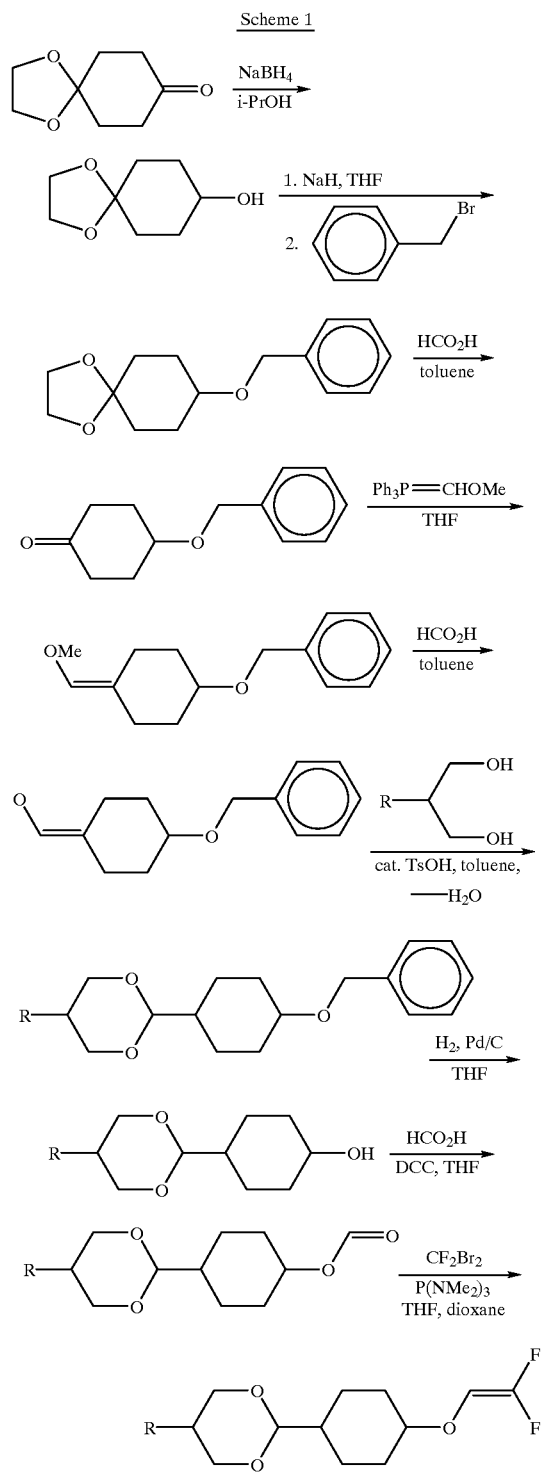

Scheme 2

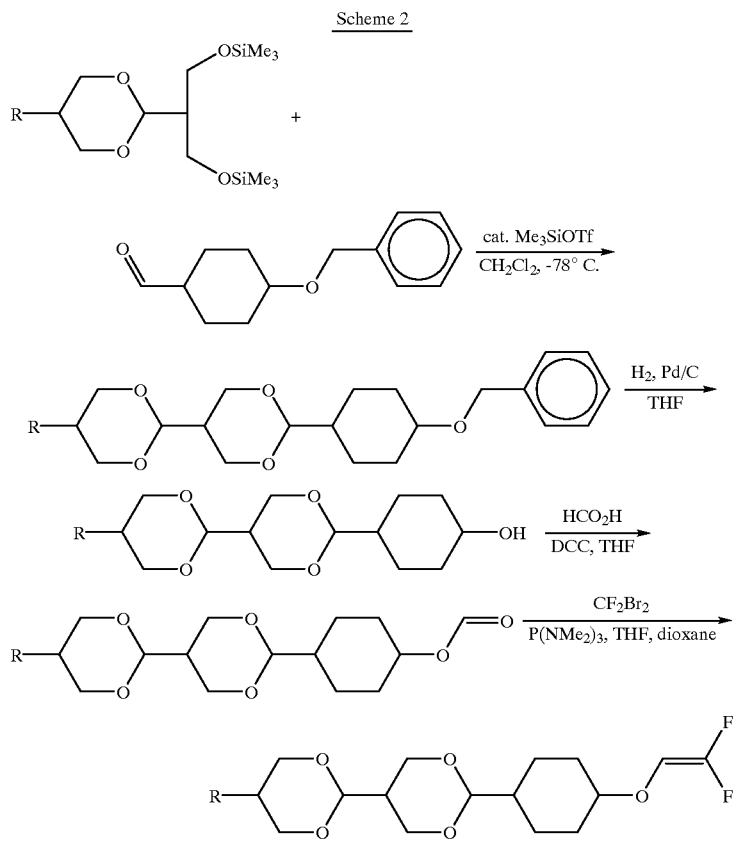

The novel liquid-crystalline media preferably comprise 2 to 40, in particular 4 to 30, components as further constituents besides one or more novel compounds. These media very particularly preferably comprise 7 to 25 components besides one or more novel compounds. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, trans-1,2-dicyclohexylethenes, 1-phenyl-2-cyclohexylethanes, 1-cyclohexyl-2-(4-phenylcyclohexyl)ethanes, trans-1-cyclohexyl-2-(4-phenylcyclohexyl)ethenes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4, 5 and 6:

| | |
|---|---|
| R'-L-E-R" | 1 |
| R'-L-COO-E-R" | 2 |
| R'-L-OOC-E-R" | 3 |
| R'-L-CH$_2$CH$_2$-E-R" | 4 |
| R'-L-C≡C-E-R" | 5 |
| R'-L-CH=CH-E-R" | 6 |

In the formulae 1, 2, 3, 4, 5 and 6, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

In the case of the compounds of the formula 6, the rings L and E which are linked directly to the CH=CH group are each -Cyc-.

One of the radicals L and E is preferably Cyc, Phe or Pyr. E is preferably Cyc, Phe or Phe-Cyc. The novel media preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-,

- Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, - G-Phe- and -G-Cyc-.

In a smaller sub-group of the compounds of the formulae 1, 2, 3, 4, 5 and 6, R' and R" are in each case, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a, 5a and 6a. In most of these compounds, R' and R" are different from one another, one of these radicals usually being alkyl, alkenyl, alkoxy or alkoxyalkyl.

In another smaller sub-group of the compounds of the formulae 1, 2, 3, 4, 5 and 6 which is known as group B, R" is —F, —Cl, —NCS or —(O)$_i$CH$_{3-(k+l)}$F$_k$Cl$_l$, where i is 0 or 1, and k+l is 1, 2 or 3; the compounds in which R" has this meaning are labelled with the sub-formulae 1b, 2b, 3b, 4b, 5b and 6b. Particular preference is given to those compounds of the sub-formulae 1b, 2b, 3b, 4b, 5b and 6b in which R" is —F, —Cl, —NCS, —CF$_3$, —OCHF$_2$ or —OCF$_3$.

In the compounds of the sub-formulae 1b, 2b, 3b, 4b, 5b and 6b, R' is as defined for the compounds of the sub-formulae 1a–6a and is preferably alkyl, alkenyl, alkoxy or alkoxyalkyl.

In a further smaller sub-group of the compounds of the formulae 1, 2, 3, 4, 5 and 6, R" is —CN; this sub-group is known as group C below, and the compounds of this sub-group are correspondingly described by sub-formulae 1c, 2c, 3c, 4c, 5c and 6c. In the compounds of the sub-formulae 1c, 2c, 3c, 4c, 5c and 6c, R' is as defined for the compounds of the sub-formulae 1a–6a and is preferably alkyl, alkoxy or alkenyl.

In addition to the preferred compounds of groups A, B and C, other compounds of the formulae 1, 2, 3, 4, 5 and 6 having other variants of the proposed substituents are also customary. All these substances can be obtained by methods which are known from the literature or analogously thereto.

Besides novel compounds of the formula I, the novel media preferably comprise one or more compounds selected from group A and/or group B and/or group C. The proportions by weight of the compounds from these groups in the novel media are preferably:

Group A: 0 to 90%, preferably 20 to 90%, in particular 30 to 90%

Group B: 0 to 80%, preferably 10 to 80%, in particular 10 to 65%

Group C: 0 to 80%, preferably 5 to 80%, in particular 5 to 50%, the sum of the proportions by weight of the group A and/or B and/or C compounds present in the particular novel media preferably being 5%–90% and in particular 60% to 90%.

The novel media preferably comprise 1 to 40%, particularly preferably 5 to 30%, of novel compounds. Further preferred media are those which comprise more than 40%, in particular 45 to 70%, of novel compounds. The media preferably comprise three, four or five novel compounds.

The novel media are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

In the foregoing and in the following examples, all temperatures are set forth uncorrected in degrees Celsius; and, unless otherwise indicated, all parts and percentages are by weight.

The entire disclosures of all applications, patents and publications, cited above and below, and of corresponding German application No. 196 54 487.4, filed Dec. 27, 1996, are hereby incorporated by reference.

EXAMPLES

In the present application and in the examples below, the structures of the liquid-crystal compounds are indicated by acroynms, the transformation into chemical formulae taking place in accordance with Tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is indicated. In each individual case, the acronym for the parent structure is followed, separated by a hyphen, by a code for the substituents $R^1$, $R^2$, $L^1$, $L^2$ and $L^3$:

| Code for $R^1$, $R^2$, $L^1$, $L^2$ and $L^3$ | $R^1$ | $R^2$ | $L^1$ | $L^2$ | $L^3$ |
| --- | --- | --- | --- | --- | --- |
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| n | $C_nH_{2n+1}$ | CN | H | H | H |
| nN.F | $C_nH_{2n+1}$ | CN | H | F | H |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |

| Code for $R^1$, $R^2$, $L^1$, $L^2$ and $L^3$ | $R^1$ | $R^2$ | $L^1$ | $L^2$ | $L^3$ |
| --- | --- | --- | --- | --- | --- |
| nF.F | $C_nH_{2n+1}$ | F | H | F | H |
| nCF$_3$ | $C_nH_{2n+1}$ | CF$_3$ | H | H | H |
| nOCF$_3$ | $C_nH_{2n+1}$ | OCF$_3$ | H | H | H |
| nOCF$_2$ | $C_nH_{2n+1}$ | OCHF$_2$ | H | H | H |
| nS | $C_nH_{2n+1}$ | NCS | H | H | H |
| rVsN | $C_rH_{2r+1}$—CH=CH— | CN | H | H | H |
| nOmFF | $C_nH_{2n+1}$ | $OC_mH_{2m+1}$ | F | F | H |
| nF.F F | $C_nH_{2n+1}$ | F | F | H | F |
| n-OXF | $C_nH_{2n+1}$ | OCH=CF$_2$ | H | H | H |
| nOCF$_3$.F.F | $C_nH_{2n+1}$ | OCF$_3$ | F | H | F |

TABLE A

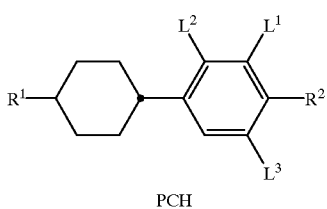

PCH

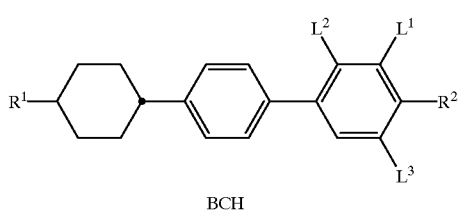

BCH

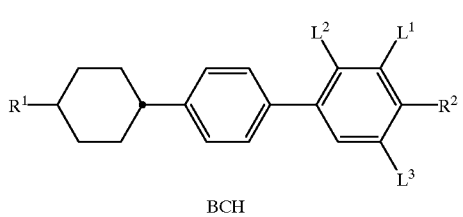

BCH

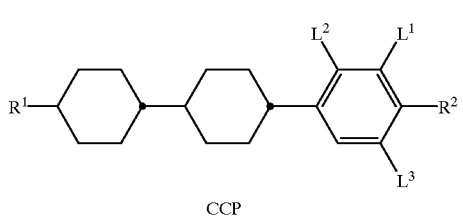

CCP

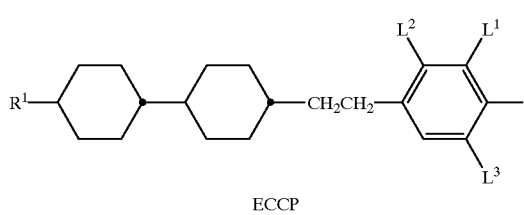

ECCP

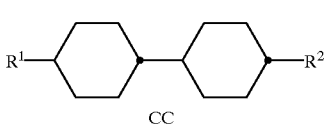

CC

TABLE B

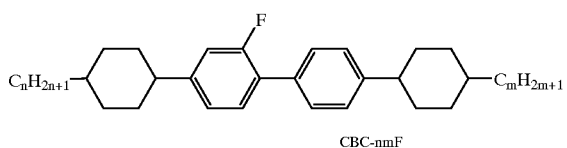

CBC-nmF

TABLE B-continued

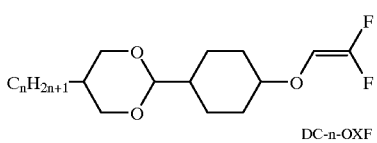

DC-n-OXF

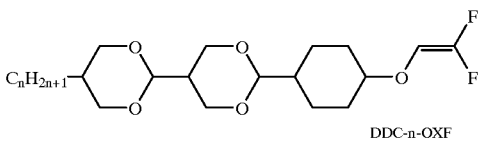

DDC-n-OXF

The examples below are intended to illustrate the invention without representing a limitation. Above and below, percent data are percent by weight. All temperatures are given in degrees Celsius. mp.=melting point, cp.=clearing point. Furthermore, C=crystalline state, N=nematic phase, Sm=smectic phase and I=isotropic phase. The number between these symbols indicates the conversion temperature. An denotes optical anisotropy (589 nm, 20° C.), and the viscosity (mm²/sec) was determined at 20° C.

"Conventional work-up" means that water is added if necessary, the mixture is extracted with dichloromethane, diethyl ether, or toluene, the organic phase is separated off, dried and evaporated, and the product is purified by distillation under reduced pressure or crystallization and/or chromatography. The following abbreviations are used:

| | |
|---|---|
| DMEU | 1,3-dimethyl-2-imidazoldinone |
| POT | potassium tert-butoxide |
| THF | tetrahydrofuran |
| pTsOH | p-toluenesulphonic acid |
| HMPT | hexamethyltriaminophosphite |
| THF | tetrahydrofuran |
| DMAP | 4-(N,N-dimethylamino)pyridine |
| DCC | dicyclohexylcarbodiimide |

EXAMPLES

Example 1

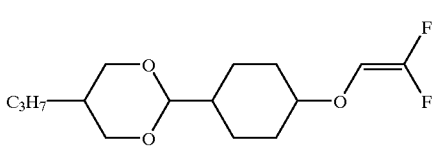

Step 1.1

A 1.5 mol of 1,4-cyclohexanedione monoethylene ketal in 800 ml of ethanol are added with stirring to 0.8 mol of sodium borohydride in 700 ml of ethanol. The mixture is stirred overnight, water is added, and the mixture is stirred for a further hour. The suspension is filtered, and the filtrate is evaporated. The residue is boiled, with stirring, with 1000 ml of methyl tert-butyl ether and 500 ml of 20% sodium acetate solution containing 30 ml of glacial acetic acid. Finally, the organic phase is separated off and subjected to conventional work-up.
Step 1.2

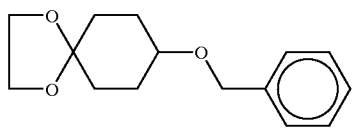
B 1.4 mol of NaH (60%) in 1000 ml of THF are heated to 40° C., and 1.06 mol of A from Step 1.1 are added with stirring. The mixture is boiled at 65° C. for 3 hours, and 1.1 mol of benzyl bromide are added dropwise to the reaction solution. The mixture is then stirred overnight at 65° C. The reaction mixture is cooled to 0° C. and hydrolysed using 3 l of water. The organic phase is separated off, and the aqueous phase is extracted with methyl tert-butyl ether. Finally, the product is subjected to conventional work-up.
Step 1.3

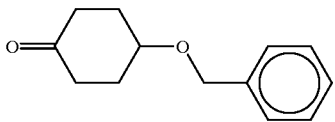
C 0.81 mol of B, 725 ml of formic acid and 1500 ml of toluene are stirred overnight at room temperature. The mixture is subsequently diluted with water, and the organic phase is separated off and subjected to conventional work-up. The crude product is purified by fractional vacuum distillation.
b.p.: 135–138° C. (0.1 mmHg)
Step 1.4

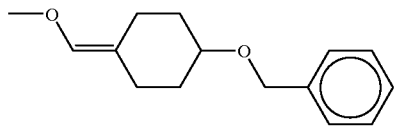
D 0.77 mol of C and 1.0 mol of methoxymethyltriphenylphosphonium chloride are dissolved in 1300 ml of THF at 5° C. under a nitrogen atmosphere. 1.0 mol of potassium tert-butoxide dissolved in 700 ml of THF is added dropwise with stirring. The mixture is stirred at room temperature for 48 hours and hydrolysed. The organic phase is separated off, and the aqueous phase is extracted a number of times with methyl tert-butyl ether. The combined organic extracts are then subjected to conventional work-up.
Step 1.5

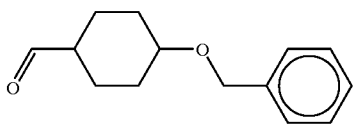
E 0.77 mol of D, 900 ml of THF and 470 ml of dilute HCl are refluxed for 3 hours. After the reaction mixture has been cooled to room temperature, the organic phase is separated off and subjected to conventional work-up. The product is recrystallized from heptane/ethyl acetate.
Step 1.6

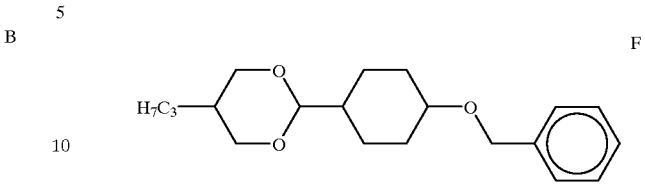
F 0.25 mol of E, 0.25 mol of 2-(n-propyl)propane-1,3-diol, 1.0 g of p-toluenesulphonic acid and 600 ml of toluene are heated on a water separator for 2 hours.

When the reaction is complete, the reaction mixture is allowed to cool to room temperature and is washed with water, and the organic phase is separated off and evaporated.

The crude product is purified by chromatography (petroleum ether/ethyl acetate=9.5:0.5). Finally, the product is recrystallized from n-hexane.
Step 1.7

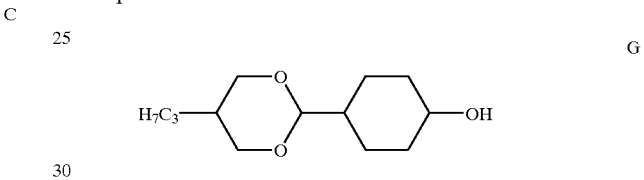
G 0.054 mol of F in 250 ml of THF are hydrogenated in the presence of 4.0 g of Pd/C (5%). When the hydrogenation is complete, the solution is evaporated, and the crude product is recrystallized from ethyl acetate.
Step 1.8

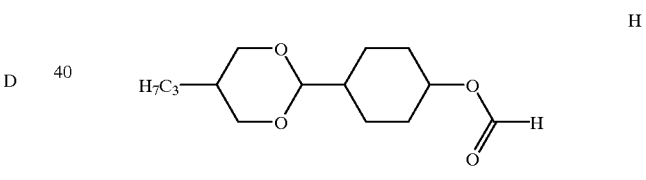
H 0.05 mol of formic acid is added at 5° C. with stirring to 0.05 mol of G, 0.055 mol of DCC and 0.005 mol of DMAP in 250 ml of dichloromethane. The mixture is stirred at room temperature for 4 hours, and the suspension is filtered. The filtrate is evaporated, and the crude product is recrystallized from pentane.
Step 1.9

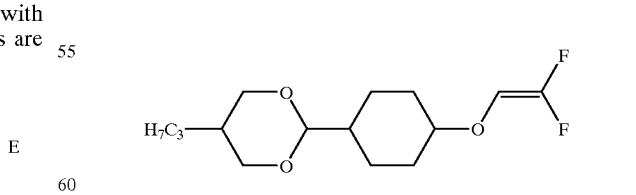
I 0.035 mol of H are dissolved in 25 ml of THF and 250 ml of dioxane, and the solution is cooled to 0°C. 0.07 mol of dibromodifluoromethane is added, and 0.14 mol of hexamethyltriaminophosphine is added dropwise at 5° C. with stirring. The reaction mixture is stirred overnight and then poured into 1000 ml of water.

Finally, the mixture is subjected to conventional work-up. The crude product is recrystallized from pentane.

Δn=+0.010; Δε=10.55

The following compounds of the formula

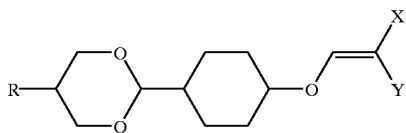

are prepared analogously:

| R | X | Y | |
|---|---|---|---|
| CH₃ | F | F | |
| C₂H₅ | F | F | |
| n-C₄H₉ | F | F | |
| n-C₅H₁₁ | F | F | Δn = +0.021; Δε = 9.74 |
| n-C₆H₁₃ | F | F | |
| CH₂=CH | F | F | |
| CH₃CH=CH | F | F | |
| CH₃ | Cl | Cl | |
| C₂H₅ | Cl | Cl | |
| n-C₄H₉ | Cl | Cl | |
| n-C₅H₁₁ | Cl | Cl | |
| n-C₆H₁₃ | Cl | Cl | |
| CH₂=CH | Cl | Cl | |
| CH₃CH=CH | Cl | Cl | |
| CH₃ | H | F | |
| C₂H₅ | H | F | |
| n-C₃H₇ | H | F | |
| n-C₄H₉ | H | F | |
| n-C₅H₁₁ | H | F | |
| n-C₆H₁₃ | H | F | |
| CH₂=CH | H | F | |
| CH₃CH=CH | H | F | |
| CH₃ | H | Cl | |
| C₂H₅ | H | Cl | |
| n-C₃H₇ | H | Cl | |
| n-C₄H₉ | H | Cl | |
| n-C₅H₁₁ | H | Cl | |
| n-C₆H₁₃ | H | Cl | |
| CH₂=CH | H | Cl | |
| CH₃CH=CH | H | Cl | |
| CH₃ | Cl | F | |
| C₂H₅ | Cl | F | |
| n-C₃H₇ | Cl | F | |
| n-C₄H₉ | Cl | F | |
| n-C₅H₁₁ | Cl | F | |
| n-C₆H₁₃ | Cl | F | |
| CH₂=CH | Cl | F | |
| CH₃CH=CH | Cl | F | |

MIXTURE EXAMPLES

Example A

| | | | |
|---|---|---|---|
| PCH—5F | 9.0% | Clearing point: | 76.5° C. |
| PCH—6F | 7.2% | Δn [589 nm; 20° C.]: | 0.0886 |
| PCH—7F | 5.4% | Δε [1 kHz; 20° C.]: | 7.06 |
| CCP—20CF₃ | 7.2% | ν₂₀° C.: | 15.0 mm²s |
| CCP—30CF₃ | 10.8% | | |
| CCP—40CF₃ | 8.1% | | |
| CCP—50CF₃ | 8.1% | | |
| BCH—3F.F | 10.8% | | |
| BCH—5F.F | 9.0% | | |
| ECCP—30CF₃ | 4.5% | | |
| ECCP—50CF₃ | 4.5% | | |
| CBC—33F | 1.8% | | |
| CBC—35F | 1.8% | | |
| CBC—55F | 1.8% | | |
| DC—5OXF | 10.0% | | |

Example B

| | | | |
|---|---|---|---|
| PCH—5F | 9.0% | Clearing point: | 78.1° C. |
| PCH—6F | 7.2% | Δn [589 nm; 20° C.]: | 0.0886 |
| PCH—7F | 5.4% | Δε [1 kHz; 20° C.]: | 6.33 |
| CCP—20CF₃ | 7.2% | ν₂₀° C.: | 15.0 mm²s |
| CCP—30CF₃ | 10.8% | | |
| CCP—40CF₃ | 8.1% | | |
| CCP—50CF₃ | 8.1% | | |
| BCH—3F.F | 10.8% | | |
| BCH—5F.F | 9.0% | | |
| ECCP—30CF₃ | 4.5% | | |
| ECCP—50CF₃ | 4.5% | | |
| CBC—33F | 1.8% | | |
| CBC—35F | 1.8% | | |
| CBC—55F | 1.8% | | |
| DC—5OXF | 10.0% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A halovinyloxy-substituted dioxane compound of the formula I

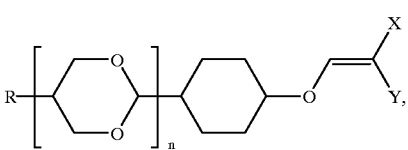

in which

R is alkyl or alkenyl having 1 to 12 carbon atoms, in each of which one or more CH₂ groups are optionally replaced by —O—, —CF₂— or —CH=CH—, and/or one or two CH groups are optionally replaced by CF, in such a way that two oxygen atoms are not linked to one another, X and Y are each, independently of one another, H, F or Cl, provided that, if one of the radicals X or Y is H, the other radical X or Y is F or Cl, and n is 1, 2 or 3.

2. A halovinyl substituted dioxane compound of claim 1 which is of the formula Ia

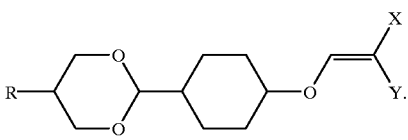

3. A halovinyloxy-substituted dioxane compound according to claim 1, wherein R is a straight-chain alkyl radical.

4. A halovinyloxy-substituted dioxane compound according to claim 2, wherein R is a straight-chain alkyl radical.

5. A halovinyloxy-substituted dioxane compound according to claim 1, wherein X and Y are F.

6. A halovinyloxy-substituted dioxane compound according to claim 2, wherein X and Y are F.

7. A halovinyloxy-substituted dioxane compound according to claim 3, wherein X and Y are F.

8. A halovinyloxy-substituted dioxane compound according to claim 1, wherein the X and Y pair are F and F, H and F, H and Cl, Cl and Cl or F and Cl.

9. A liquid-crystalline medium having at least two liquid-crystalline components, wherein at least one component is a compound of the formula I according to claim 1.

10. An electro-optical display which comprises a liquid-crystalline medium according to claim 9.

11. A halovinyl substituted dioxane compound of claim 1 of the formula Ib:

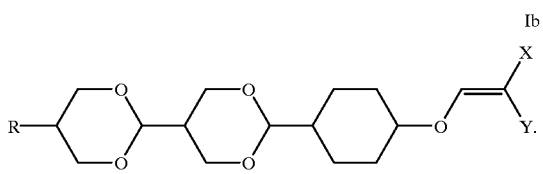

12. A halovinyl substituted dioxane compound of claim 1, wherein R is 1E-alkenyl, 3-alkenyl, $C_nH_{2n+1}$—(CH=CH)$_o$, $CF_2$=CH—O— or $CF_2$=CF—, where n=1–8 and o is 0 or 1.

13. A halovinyl substituted dioxane compound of claim 1, wherein R is an optically active branched group.

14. The liquid-crystalline medium of claim 9, which comprises 1 to 40% by weight of compounds of the formula I of claim 1.

15. The liquid-crystalline medium of claim 9, which comprises 44 to 70% by weight of compounds of the formula I of claim 1.

16. A halovinyl substituted dioxane compound of claim 1, wherein the compound has a $\Delta n$ of 0.021 or lower.

17. A halovinyl substituted dioxane compound of claim 1, wherein the compound has a $\Delta\epsilon$ of 9.74 or higher.

18. A halovinyl substituted dioxane compound of claim 1, wherein the compound has a $\Delta n$ of 0.021 or lower and a $\Delta\epsilon$ of 9.74 or higher.

* * * * *